United States Patent [19] [11] 4,315,988
Miwa et al. [45] Feb. 16, 1982

[54] THERMOPHILIC COLLAGENASES, THERMOPHILIC BACTERIA CAPABLE OF PRODUCING THERMOPHILIC COLLAGENASES, AND PROCESS FOR PRODUCING SAID COLLAGENASES

[75] Inventors: Naoto Miwa, Ami; Yoshiro Masuda, Kashiwa; Seiichi Kawarabuki; Toshiyuki Sai, both of Ami; Takao Saito, Tsuchiura, all of Japan

[73] Assignee: Mitsubishi Petrochemical Co., Ltd., Tokyo, Japan

[21] Appl. No.: 25,748

[22] Filed: Mar. 30, 1979

[30] Foreign Application Priority Data

Mar. 30, 1978 [JP] Japan .................................. 53-36018

[51] Int. Cl.$^3$ .......................... C12N 9/54; C12N 1/20
[52] U.S. Cl. .................................... 435/221; 435/832; 435/253
[58] Field of Search ........................... 435/219–222, 435/253

[56] References Cited

U.S. PATENT DOCUMENTS 3,267,006  8/1966  Hakim et al. ....................... 435/226

OTHER PUBLICATIONS

Chemical Abstracts, vol. 87, 1977: 197039v.
Chemical Abstracts, vol. 92, 1980: 54005y.
Biochim. Biophys. Acta, vol. 122 (1966), pp. 557–559.
Biochemistry, vol. 3, No. 11, 1964, pp. 1737–1741.

Primary Examiner—Lionel M. Shapiro
Attorney, Agent, or Firm—Wenderoth, Lind & Ponack

[57] ABSTRACT

This invention relates to a process for producing collagenase, which comprises aerobically cultivating a collagenase-producing bacterium belonging to the genus Bacillus, and recovering collagenase from the culture broth.

This invention also provides a thermophilic bacterium of the genus Bacillus which has the ability to produce collagenase and which grows at a temperature of 42° to 74° C. and a pH of 5.0 to 9.0 and a novel thermophilic collagenase which does not substantially lose collagenase activity even when maintained for 1 hour at a temperature of 60° C. in the presence of a calcium ion at a pH in the range of 6.5 to 8.5, and which has a molecular weight, determined by gel filtration, between those of cytochrome C and ovalbumin.

14 Claims, 7 Drawing Figures

THERMOPHILIC COLLAGENASES, THERMOPHILIC BACTERIA CAPABLE OF PRODUCING THERMOPHILIC COLLAGENASES, AND PROCESS FOR PRODUCING SAID COLLAGENASES

This invention relates to a novel process for producing collagenase; novel thermophilic collagenase produced by said process; and to novel thermophilic bacteria of the genus Bacillus capable of producing thermophilic collagenase.

Collagenase is an enzyme capable of decomposing collagen which is a protein making up the connective tissues or skin of mammals, etc. This enzyme has aroused great interest, and found applications in various fields because
 (1) it removes nacrotic tissues caused by ulcers or burns, and incites growth of normal tissues;
 (2) it decomposes the connective tissues connecting the cells of the animal tissues to prepare a cell floating solution; or
 (3) it can be used for the determination of the arrangement of amino acids in a protein or polypeptide by utilizing its high substrate specificity.

To the best of the knowledge of the present inventors, a method for producing collagenase using bacteria of the genus Clostridium (Biochemistry 3, 1737 (1964)) and a method for producing collagenase using bacteria of the genus Pseudomonas (Biochimica Biophysica Acta, 122, 557 (1966)) are the only known methods for the production of collagenase.

The latter is not used commercially because the ability of the bacterial strain to produce collagenase is far lower than that of the bacteria of the genus CLostridium in the former. The method using the bacteria of the genus Clostridium, however, is used to produce collagenases now on the market.

The bacteria of the genus Clostridium are pathogenic bacteria which cause gaseous edema, tetanus, etc., and the method using these bacteria is very dangerous to health. Furthermore, since the bacteria of the genus Clostridium grow anaerobically, special designs in equipment are required for commercial cultivation. This method also has the disadvantage that the cultivation must be carried out in the presence of a reducing agent.

Collagenases produced by the bacteria of the genus Clostridium are active at ordinary temperatures (30° to 40° C.), but lose activity at relatively high temperatures. For this reason, it is necessary, for example, to perform fixation at a low temperature so as to prevent deactivation by the heat of reaction at the time of fixation. Their handling also requires great care because they will be deactivated with modifying agents, etc. used for the fixation.

It is an object of this invention to provide a process for producing collagenases of high activity under aerobic conditions using collagenase-producing bacteria of the genus Bacillus.

To the best of the knowledge of the present inventors, the production of collagenase by bacteria of the genus Bacillus was quite unknown prior to the present invention.

The work of the present inventors has shown that aerobic, thermophilic bacteria of the genus Bacillus can produce thermophilic collagenases which are quite different from the conventional collagenases.

It is another object of this invention therefore to provide novel thermophilic collagenases.

Still another object of this invention is to provide novel collagenase-producing bacterial strains of the genus Bacillus which can produce such novel thermophilic collagenases.

Other objects and advantages of this invention will become more apparent from the following description.

The novel process for producing collagenase in accordance with this invention comprises aerobically cultivating a collagenase-producing bacterial strain of the genus Bacillus in a culture medium, and recovering collagenase from the culture broth.

The collagenase-producing bacteria of the genus Bacillus denote bacteria of the genus Bacillus which will produce collagenase in the culture broth when aerobically cultivated.

Cultivation in accordance with this invention is usually carried out in a liquid medium. Various nutrient sources are used in the culture medium. Natural nutrient sources such as peptone, yeast extract and corn steep liquor are preferred because they favorably affect the growth of these bacteria.

The cultivation temperature and the pH of the culture medium vary depending upon the bacterial strain used. Since the cultivation is carried out aerobically, the culture medium is preferably agitated by passing air into it.

The method of this invention using novel strains of the genus Bacillus isolated for the first time by the present inventors will be described below in detail.

The present inventors successfully obtained the following three bacterial strains of the genus Bacillus by isolation and screening.
 (1) Bacillus sp. nov. MY-101 (MY-101 for short),
 (2) Bacillus sp. nov. MY-102 (MY-102 for short),
 (3) Bacillus sp. nov. MY-103 (MY-103 for short).

These three strains, MY-101, MY-102 and MY-103, were deposited on March 27, 1978 at Fermentation Research Institute (FRI), Agency of Science and Technology, Japan under deposit numbers FERM-P4442, FERM-P4443 and FERM-P4444. Samples of these microorganisms which are on deposit at FRI have been forwarded by FRI to American Type Culture Collection (ATCC), Rockville, Md., U.S.A. for accession into the ATCC collection.

The microorganisms have been accessioned into the ATCC colltion under the following accession numbers:
 FERM-P4442—ATCC No. 31505,
 FERM-P4443—ATCC No. 31506,
 FERM-4444—ATCC No. 31507.

The present inventors determined the bacteriological properties of MY-101, MY-102 and MY-103 as follows:

| I. | Microscopic observations | | | |
|---|---|---|---|---|
| | | MY-101 | MY-102 | MY-103 |
| | 1. Morphology | Rods 0.5–0.8 × 2.0–6.0μ | Rods 0.4–0.8 × 1.5–6.0μ | Rods 0.5–0.8 × 2.0–10μ |
| | 2. Plemorphism | No | No | No |
| | 3. Motility | Yes | Yes | Yes |
| | 4. Flagella | Present | Present | Present |
| | 5. Flagellation | Polar | Polar | Polar |
| | 6. Gram stain | Negative | Negative | Negative |
| | 7. Spores | Formed | Formed | Formed |
| | 8. Sporangia | Elliptical | Elliptical | Elliptical |
| | 9. Site of spores | End | End | End |

-continued

II. Cultural characteristics on an agar slant (cultivated at 55° C. for one day on bouillon agar)

| | MY-101 | MY-102 | MY-103 |
|---|---|---|---|
| 1. Growth | Good | Good | Good |
| 2. Gloss | Yes | Yes | Yes |
| 3. Color | Colorless | Colorless | Colorless |
| 4. Color of medium | No change | No change | No change |

III. Cultural characteristics on an agar plate (same as in II)

| | MY-101 | MY-102 | MY-103 |
|---|---|---|---|
| 1. Shape | Circular | Circular | Circular |
| 2. Surface | Smooth | Smooth | Smooth |
| 3. Peripheral edge | Entire | Undulate | Entire |
| 4. Protrusion | Flat | Conical | Conical |
| 5. Optical characteristics | Non-transparent | Non-transparent | Non-transparent |

IV. Cultural characteristics in surface cultivation (stationary cultivation at 55° C. for 1 day on a bouillon medium)

| | MY-101 | MY-102 | MY-103 |
|---|---|---|---|
| 1. Growth on surface | Pellicle formed | Pellicle formed | Pellicle not formed |
| 2. Coloration and decolorization | No | No | No |
| 3. Turbidity | Yes | Slight | No |
| 4. Sediment | Yes | Yes | Yes |

V. Physiological characteristics

| | MY-101 | MY-102 | MY-103 |
|---|---|---|---|
| 1. Growth temperature (°C.) | 42–74 | 45–70 | 45–70 |
| 2. Growth pH | 5.0–9.0 | 5.0–9.0 | 5.0–8.5 |
| 3. Oxygen demand | Aerobic | Aerobic | Aerobic |
| 4. Gelatin liquefaction (*1) | Yes | Yes | Yes |
| 5. Litmus milk | Liquefied | Liquefied | No change |
| 6. Indol production | No | No | No |
| 7. Reduction of nitrate | No | No | No |
| 8. MR test | Negative | Negative | Negative |
| 9. VP test | Negative | Negative | Negative |
| 10. Production of hydrogen sulfide | Yes | Yes | Yes |
| 11. Hydrolysis of starch | Yes | No | No |
| 12. Utilization of citric acid | No | No | No |
| 13. Urease | Positive | Negative | Negative |
| 14. Oxidase | Negative | Negative | Negative |
| 15. Catalase | Negative | Negative | Negative |
| 16. Utilization of sugard (*2) | | | |
| Glucose | + | + | + |
| Maltose | + | + | + |
| Arabinose | + | + | + |
| Xylose | + | + | + |
| Trehalose | − | − | + |
| Salicin | − | + | + |
| Saccharose | − | − | − |
| Lactose | − | − | + |
| Sorbitol | − | − | − |
| Inositol | − | − | − |
| Mannitol | − | − | − |

(*1): Shaking culture was performed at 65° C. for 2 days in a culture medium (adjusted to pH 6.5) composed of 0.1 g/l of $KH_2PO_4$, 0.25 g/l of $K_2HPH_4$, 0.2 g/l of $(NH_4)_2SO_4$, 0.2 g/l of NaCl, 0.11 g/l of $CaCl_2$, 0.2 g/l of $MgCl_2 \cdot 6H_2O$, 0.2 g/l of $MnCl_2 \cdot 4H_2O$, 0.5 g/l of corn steel liquor and 30% by weight of gelatin. The culture broth was rapidly cooled to determined whether it solidified.
(*2): Biotest disks of Eiken Chemical Co., Ltd. were used.

The above bacteriological properties were compared with the descriptions of Bergey's Manual of Determinative Bacteriology, 7th edition (1957) and 8th edition (1974) (Williams & Wilkins Co.). This led to the conclusion that these bacterial strains belong to the genus Bacillus.

*Bacillus stearothermophilus* has long been knwon as a strain which can be grown at high temperatures. This strain, however, has different physiological properties from the three strains given above in that it does not liquefy gelatin. Moreover, this strain does not produce collagenase, and is thus different from the three strains isolated by the present inventors.

It has been found that the three strains MY-101, MY-102 and MY-103 are novel strains belonging to the genus Bacillus, and when cultivated, produce collagenase in the culture broth.

A preferred embodiment of this invention, therefore, is a process for producing collagenase using aerobic collagenase-producing bacteria of the genus Bacillus which grow at a pH of 5.0 to 9.0, preferably 5.0 to 8.5, and a temperature of 42° to 74° C., preferably 45° to 70° C., above all the strains MY-101, MY-102 and MY-103 isolated for the first time by the present inventors.

Desirably, the cultivation temperature and the pH of the culture medium for these novel strains should be adjusted to the aforesaid ranges used to specify these strains. Generally, the suitable cultivation temperature is 40° to 75° C., preferably 50° to 70° C., and the pH of the culture medium is preferably 6 to 8.5 at the beginning of cultivation.

The present inventors have also found that these collagenase-producing strains belonging to the genus Bacillus have the ability to assimilate polypeptides containing glycine units and proline units, for example collagen or gelatin.

Surprisingly, it has been found that that the yield of collagenase increases when the cultivation in accordance with this invention is carried out in the presence of a polypeptide containing glycine units and proline units, preferably collagen or gelatin, especially the latter, added to the culture medium.

At the cultivation temperatures of general microorganisms which grow at ordinary temperatures, a liquid medium containing gelatin solidifies to a gel, and thus cannot be used as a substrate for cultivation under aeration. However, in the cultivation of the thermophilic bacteria such as the strain MY-101 of this invention having an optimal growth temperature at 60° to 70° C., the gelatin-containing medium remains liquid without solidification, and therefore can be used a substrate for cultivation under aeration. The yield of collagenase can be increased in this case over the case of not using gelatin or the like. For example, when the strain MY-101 is used, the yield of collagenase increases with increasing gelatin concentration up to 40%.

In performing the process of this invention, a divalent metal ion may further be caused to be present in the culture medium. Preferred divalent metal ions are, for example, $Ca^{2+}$, $Mg^{2+}$ and $Mn^{2+}$, and they are preferably added as chlorides or sulfates. These metal ions may be present singly in the culture medium, but preferably $Ca^{2+}$, $Mg^{2+}$ and $Mn^{2+}$ are caused to be present together in the culture medium. Whether these metal ions are used singly or as a combination, the concentration of each of these metallic ions is suitably 0.1 to 100 mM, preferably 1 to 70 mM, especially 10 to 50 mM. The presence of such a divalent metal ion in the culture medium increases the yield of collagenase.

For example, in the cultivation of MY-102 and MY-103, the presence of even 1 mM of the divalent metal ion will improve the yield of collagenase.

By performing the cultivation in accordance with this invention as described hereinabove, collagenase is accumulated in the culture medium. The collagenase thus accumulated in the culture medium can be separated and purified in a customary manner.

Specifically, insoluble materials such as bacterial cells are removed from the culture broth by a mechanical separating procedure such as centrifugal separation or filtration. Collagenase can be separated and purified, for example, by subjecting the supernatant liquid or filtrate (crude enzyme solution) to various chromatographic techniques such as ion exchange, gel filtration or adsorption, or to salting out with ammonium sulfate, or by treating it with an organic solvent, or by applying suitable combinations of these methods.

The collagenase obtained by the method of this invention is a useful, collagen-decomposing enzyme which can be widely used in various medical or biological fields as described at the outset of the present specification.

In particular, collagenases obtained by the cultivation of aerobic and thermophilic collagenase-producing bacteria of the genus Bacillus have an optimal growth temperature in a high temperature region and exhibit excellent enzymatic activities unlike conventional collagenases produced by bacteria of the genus Clostridium. Accordingly, these collagenase can be used in various fields within a wide temperature range unlike the conventional collagenases. Futhermore, these thermophilic collagenases have superior storage stability and are highly stable to various modifiers and the like. Thus, these enzymes do not lose activity when fixed, in contrast to the conventional collagenases which are deactivated at such a time. Accordingly, they can be used in the fixed state in various organic chemical reactions.

The present invention thus also provides the novel thermophilic collagenases as described above.

These thermophilic collagenases are specified as novel thermophilic collagenase characterized by the fact that they do not substantially lose collagenase activities even when maintained at 65° C. for 1 hour in the presence of a calcium ion at a pH of 7.2 to 7.5, and have a molecular weight intermediate between those of cytochrome C and ovalbumin.

These novel thermophillic collagenases of this invention can be produced, for example, by cultivating the novel aerobic and thermophilic bacterial strains MY-101, MY-102 and MY-103 isolated for the first time by the present inventors.

Thermophilic collagenase obtained by the cultivation of the MY-101 strain has the following properties.

1. Activity and substrate specificity

It acts on collagen, gelatin or collagen having an azo dye bonded thereto (for example, "Azocoll", a product of Calibiochem Behring Co.) to hydrolyze it.

2. Temperature dependence

Figure 1:
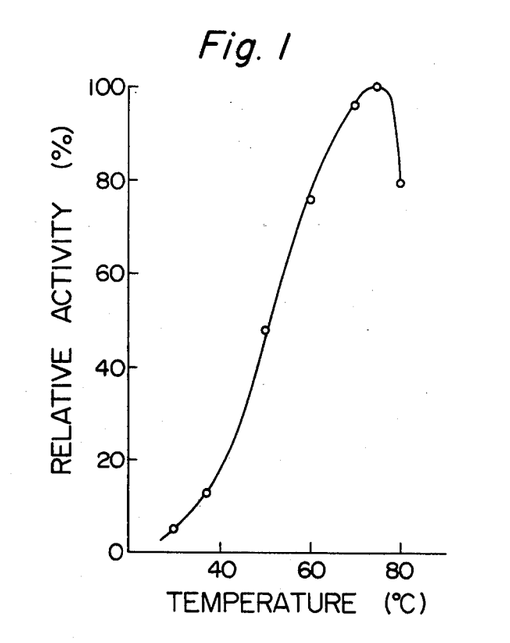

Its temperature dependence is shown in FIG. 1 of the accompanying drawings. In FIG. 1, the abscissa represents the temperature (°C.), and the ordinate, the relative activity (%) at varying temperatures which was determined by taking the maximum activity as 100. The enzyme activity was measured in 50 mM Tris-HCl buffer, pH 7.5 (determined at 25° C.), containing 1 mM $CaCl_2$ at the indicated temperature for 10 minutes.

It is seen from FIG. 1 that the collagenase of this invention is very stable to heat, and shows a maximum activity at about 75° C.

3. Heat stability

Figure 2:
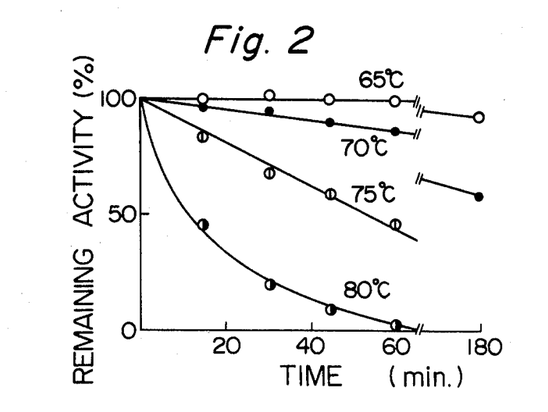

FIG. 2 of the accompanying drawings shows the heat stability of the collagenase of this invention at 65° C., 70° C., 75° C. and 80° C. in 50 mM Tris-HCl buffer, pH 7.5 (determined at 30° C.), containing 1 mM $CaCl_2$. In FIG. 2, the abscissa represents the time (minutes) during which the collagenase was maintained, and the ordinate, the remaining activity (%) of the collagenase at varying maintenance times which was determined by taking the initial activity as 100. At appropriate intervals, an aliquot of the enzyme solution was taken and its remaining activity was measured at 60° C.

FIG. 2 shows that the collagenase of this invention is very stable to heat, and scarcely loses its activity when heat-treated at 65° C. for 1 hour, and that even after the 3-hour heat-treatment, it loses only about 10% of its activity. It is also seen that by the heat-treatment at 75° C. for 3 hours, the collagenase of the invention retains about 50 to 60% of its activity, and thus loses only about 50% at most of its activity.

4. Optimal pH

Figure 3:
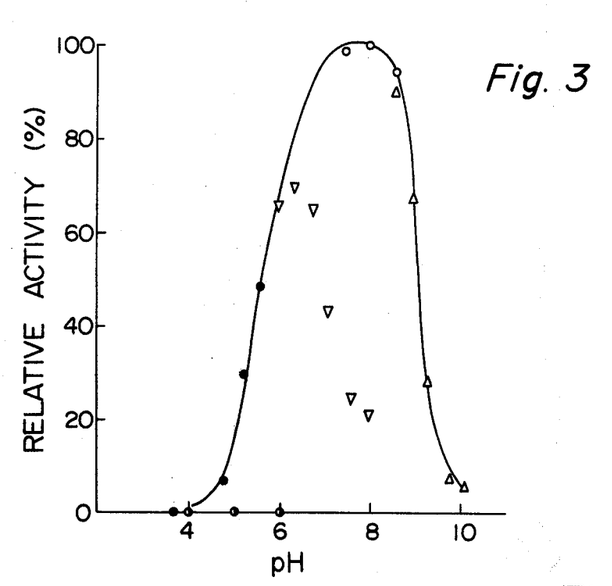

FIG. 3 of the accompanying drawings shows the pH dependence of the collagenase of this invention in the absence of a metal ion. In FIG. 3, the abscissa represents the pH at 30° C., and the ordinate, the relative activity (%) of the collagenase at varying pH values which was determined by taking the maximum activity as 100. The buffers used were (at 50 mM concentration): ◐ succinic acid/NaOH; ◑ sodium citrate/citric acid; ▽ $K_2HPO_4/KH_2PO_4$; ○ Tris/HCl; △ Gly/NaOH. The activity was measured at 60° C. for 10 minutes.

The sodium citrate/citric acid ◑ and $K_2HPO_4/KH_2PO_4$ ▽ differ from the other buffers in that they have the action of forming chelates with metal ions. When these buffers are used, the activity of collagenase is lower than in the case of using the other buffers.

FIG. 3 shows that the collagenase of this invention has an optimal pH at 6.5 to 8.5, especially at 7.2 to 8.0.

5. pH range for stability

Figure 4:
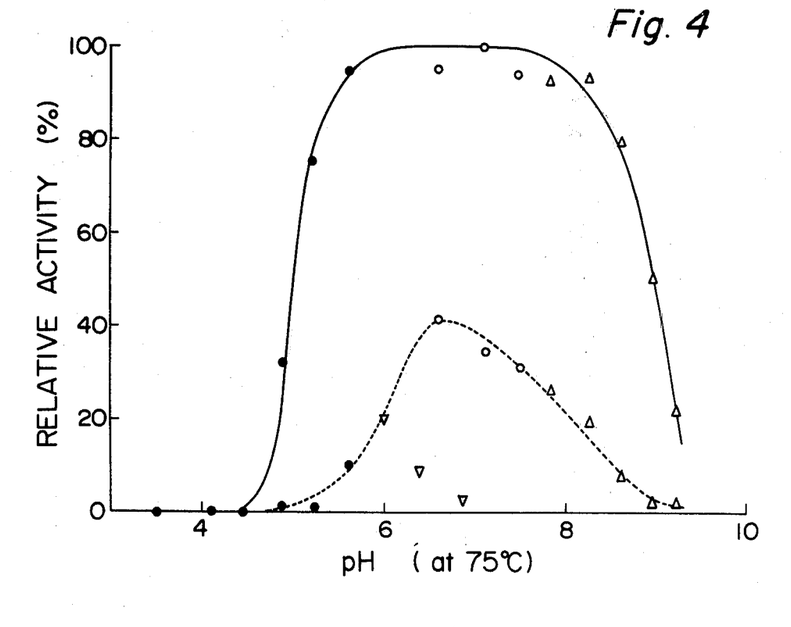

FIG. 4 of the accompanying drawings shows the pH dependence of the collagenase of this invention. In FIG. 4, the abscissa represents the pH at 75° C., and the ordinate, the relative activity (%) at varying pH values which was determined by taking the maximum activity as 100.

The pH dependence of heat stability was studied by incubating the enzyme at 75° C. for 10 minutes in buffers with or without 1 mM $CaCl_2$, followed by assaying the remaining activity in 50 mM Tris-HCl buffer, pH 7.5, containing 1 mM $CaCl_2$ at 60° C. for 10 minutes. The solid line indicates the presence of 1 mM $CaCl_2$, and the dotted line, the absence of $CaCl_2$.

It is seen from FIG. 4 that the colagenase of this invention is stable at a pH range of 5.6 to 8.5 when heat-treated for 10 minutes at 75° C. in the presence of 1 mM $CaCl_2$.

6. Activation and Inhibition

The collagenase of this invention is a metalloenzyme, and its activity is inhibited by metal chelating reagents such as ethylenediaminetetraacetic acid.

7. Molecular weight

Figure 5:
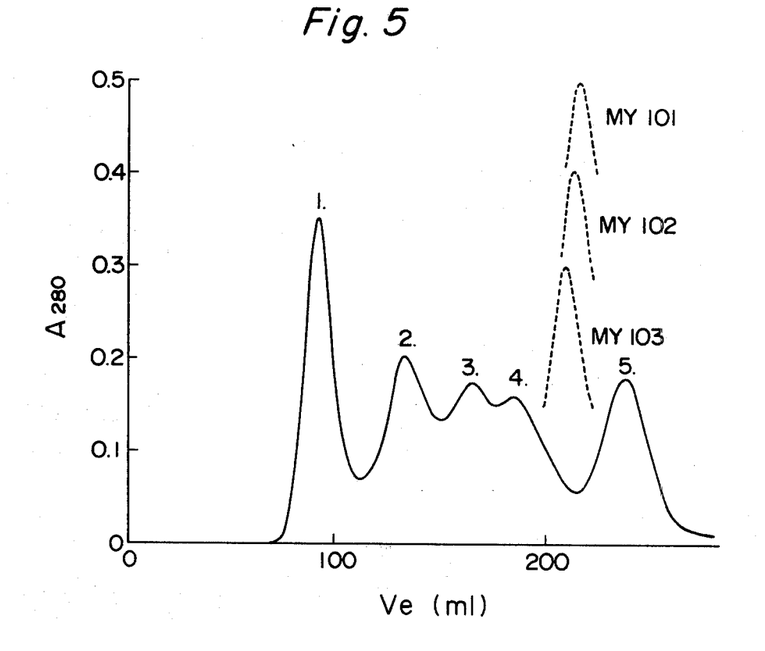

FIG. 5 of the accompanying drawings shows the results of gel filtration performed in accordance with the method of P. Andrews [Biochemical Journal (1965), Vol. 96, pages 595–606]. In FIG. 5, the abscissa represents the amount of elution (Ve, ml), and the ordinate, the absorbance ($A_{280}$) at 280 mμ. The curve in solid line in the graph shows the results obtained with internal standard proteins, and the peaks 1, 2, 3, 4 and 5 are assigned respectively to apoferritin, rabbit muscle aldolase, bovine serum albumin, ovalbumin and cytochrome C. The three peaks drawn by dotted lines are assigned to the thermophilic collagenases produced by the novel strains MY-101, MY-102, and MY-103 of this invention, respectively.

Based on the results shown in FIG. 5, a calibration curve was drawn in which the abscissa represents the molecular weight in logarithmic scale and the ordinate, the amount of elution (Ve, ml). The molecular weight of the thermophilic collagenase of this invention was determined from this calibration curve. As a result, the thermophilic collagenases of this invention have been found to have a molecular weight intermediate between those of cytochrome C and ovalbumin, and many of them have a molecular weight of 15,000 to 25,000.

Thus, the thermophilic collagenases of this invention have such a superior heat stability that they do not substantially lose their collagenase activities at their optimal pH range of 6.5 to 8.5 even when maintained for 1 hour at such a high temperature at which the conventional collagenases are not expected at all to retain activites, for example at 60° C., in the presence of a calcium ion. These collagenases are expected to be utilized medically and biologically over a broad temperature range.

The following Examples illustrate the present invention in more detail. It should be understood however that the invention is not limited to these examples.

Unless otherwise specified, the enzyme activity (potency) of collagenase described in the following Examples and elsewhere in the present application was determined by the following method.

Method of measuring potency

An L-shaped tube was charged with 10 mg of "Azocoll" and 3 ml of 50 mM Tris-HCl buffer (pH 7.5), and they were allowed to stand at 60° C. for 5 minutes. 5 to 10 µl of an enzyme solution, optionally diluted, was added to initiate reaction. After shaking the mixture at 60° C. for 5 to 10 minutes, 1.0 ml of 10% trichloroacetic acid was added to stop the reaction. The reaction mixture was filtered, and the absorbance of the filtrate at 520 nm was measured and designated AS. As a control, the mixture was shaken for the same period of time without adding the enzyme solution, and the reaction was stopped by adding trichloroacetic acid. Then, the same amount as above of the enzyme solution was added. The absorbance of the resulting solution at 520 nm was measured and designated AB.

One unit of potency is defined as the amount of the enzyme required to increase the difference (AS-AB) in absorbance between the sample and the control under the above conditions by 0.001. The potency (U) can thus be determined in accordance with the following equation.

$$U = \frac{(AS - AB) \times 1000}{\text{Reaction time in minutes}}$$

Method of measuring molecular weight

The molecular weight as measured in accordance with the method of P. Andrews [Biochemical Journal (1965), Vol. 96, pages 595–606]. Specifically, the sample was chromatographed on a column, 2.6 cm in inside diameter, packed with Sephadex G-200 (a product of Pharmacia Company, Sweden) to a height of 58 cm at an eluting speed of 13 ml/hr using as internal standard proteins of known molecular weights cytochrome C (molecular weight 12,500), ovalbumin (molecular weight 45,000), bovine serum albumin (molecular weight 67,000), rabbit muscle aldolase (molecular weight 160,000) and apoferritin (molecular weight 450,000). The results are shown in FIG. 5. The amounts of the internal standard proteins eluted were plotted against their molecular weights to draw a calibration curve. From the calibration curve, the molecular weight of collagenase was determined.

EXAMPLE 1

(A) Into a 500 ml Sakaguchi flask containing 100 ml of a culture medium composed of 0.8% of peptone, 0.4% of yeast extract and 0.3% of NaCl (adjusted to pH 7.0) was inoculated one platinum loopful of MY-101 strain which had been grown on a slant prepared by solidifying the aforesaid medium with 3% agar. Thus, pre-cultivation of the MY-101 strain was started. The pre-cultivation was performed by reciprocally shaking the flask at 65° C. for 4 to 6 hours.

(B) A 10-liter fermentor was charged with 5 liters of a culture medium (adjusted to pH 6.5) composed of 0.1 g/l of $KH_2PO_4$, 0.25 g/l of $K_2HPO_4$, 0.2 g/l of $(NH_4)_2SO_4$, 0.2 g/l of NaCl, 1.1 g/l of $CaCl_2$, 2.0 g/l of $MgCl_2.6H_2O$, 2.0 g/l of $MnCl_2.4H_2O$, 0.5 g/l of corn steep liquor and 10% of gelatin. Then, 50 ml of the pre-culture obtained in (A) was aseptically poured into the fermentor and the cultivation was started. The cultivation was performed for 60 to 80 hours at a temperature of 65° C. and an agitating speed of 600 rpm while passing air at a rate of 4 to 10 liters/min.

(C) The culture broth obtained was centrifugally separated to remove the cells. Ammonium sulfate was dissolved in the filtrate to 55% saturation, and the precipitate was aged. The supernatant liquid was removed by decantation. The precipitate was dialyzed against 10 mM Tris-HCl buffer (pH 8.6).

(D) The dialyzate was equilibrated with the aforesaid buffer, and caused to be adsorbed to DEAE-Sepharose OL-6B (a product of Pharmacia Company, Sweden) packed in a column, 5 cm in inside diameter and 1 m in length. Elution was performed with the aforesaid buffer by increasing the concentration of sodium chloride linearly from 0 to 0.8 M to obtain a DEAE-Sepharose active fraction.

(E) Ammonia sulfate was added to the eluted active fraction to 50% saturation to precipitate the resulting collagenase. The precipitate was recovered by centrifugal separation, dissolved in 50 mM Tris-HCl buffer (pH 7.5), and subjected to gel filtration by Sephadex G-100 packed in a column, 5 cm in inside diameter and 1 m in length. As an eluent, a 50 mM Tris-HCl buffer (pH 7.5) containing 0.2 M NaCl was used, and a G-100 (I) active fraction was obtained.

(F) Ammonium sulfate was added to the active fraction to 50% saturation. The precipitated collagenase was recovered by centrifugal separation, and again gel-filtered on a column of Sephadex G-100 to obtain a G-100 (II) active fraction. Thus, an enzyme sample was obtained which was uniform when determined by disc electrophoresis.

The results obtained with the cultivation filtrate in step (C) and the active fractions in steps (D), (E) and (F) are shown in Table 1. The G-100 active fraction (collagenase) obtained in step (F) had a molecular weight of 17,000 to 23,000.

TABLE 1

| Step | Amount (ml) | Protein (mg) | Activity (U/ml) | Specific activity (U/mg protein) | Total activity (U × $10^{-7}$) | Degree of purification (*) | Ratio of recovery (**) |
|---|---|---|---|---|---|---|---|
| Cultivation filtrate in step (C) | 10,000 | 530,000 | 5,890 | 111 | 5.89 | 1 | 100 |
| DEAE-Sepharose active fraction in step (D) | 3,890 | 2,900 | 10,500 | 14,100 | 4.08 | 127 | 69 |
| G-100 (I) active fraction in step (E) | 1,190 | 415 | 17,600 | 50,400 | 2.09 | 454 | 35 |
| G-100 (II) active fraction in step (F) | 770 | 85 | 21,200 | 192,000 | 1.63 | 1,730 | 28 |

(*): The degree of purification denotes the number of times of the specific activity of the active fraction based on the specific activity of the cultivation filtrate of step (C) which is taken as 1.

(**): The ratio of recovery is the percentage of the total activity of the active fraction based on the total activity of the filtrate in step (C).

EXAMPLE 2

MY-102 strain was pre-cultivated in a 500 ml Sakaguchi flask under the same conditions as described in Example 1. A 2-liter fermentor was charged with 1 liter of a culture medium (adjusted to pH 6.5) composed of 0.1 g of $KH_2PO_4$, 0.25 g of $K_2HPO_4$, 0.2 g of $(NH_4)_2SO_4$, 0.2 g of NaCl, 1.1 g of $CaCl_2$, 2.0 g of $MgCl_2.6H_2O$, 2.0 g of $MnCl_2.4H_2O$, 0.5 g of corn steep liquor and 10 g of gelatin. 10 ml of the pre-culture was aseptically poured into the fermentor, and the cultivation was started. The cultivation was performed at a temperature of 65° C. and an agitating speed of 500 rpm while passing air at a rate of 0.75 liter/min. The collagenase activity of the cultivation filtrate after cultivation for 50 to 70 hours was about 7,000 U/ml. This collagenase had a molecular weight of 18,000 to 24,000.

Figure 6:
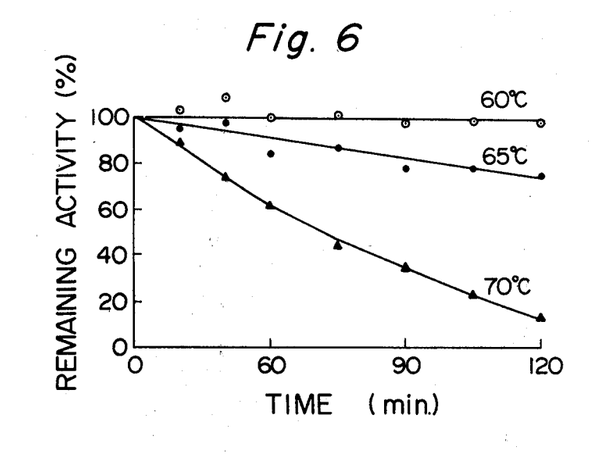

FIG. 6 of the accompanying drawings shows the heat stability at 60° C., 65° C. and 70° C. of the collagenase obtained from MY-102, which was measured by the method described hereinabove in "3. Heat stability".

EXAMPLE 3

MY-103 was pre-cultivated in a 500 ml Sakaguchi flask under the same conditions as described in Example 1. A 2-liter fermentor was charged with 1 liter of a culture medium (adjusted to pH 6.5) composed of 0.1 g of $KH_2PO_4$, 0.25 g of $K_2HPO_4$, 0.2 g of $(NH_4)_2SO_4$, 0.2 g of NaCl, 2.2 g of $CaCl_2$, 4.0 g of $MgCl_2.6H_2O$, 4.0 g of $MnCl_2.4H_2O$, 0.5 g of corn steep liquor, and 10 g of gelatin. Then, 10 ml of the pure-culture was aseptically poured into the fermentor, and the cultivation was started. When the cultivation was performed under the same conditions as in Example 2, the collagenase activity of the cultivation filtrate after cultivation for 60 to 80 hours was about 8,000 U/ml. The collagenase had a molecular weight of 19,000 to 25,000.

Figure 7:
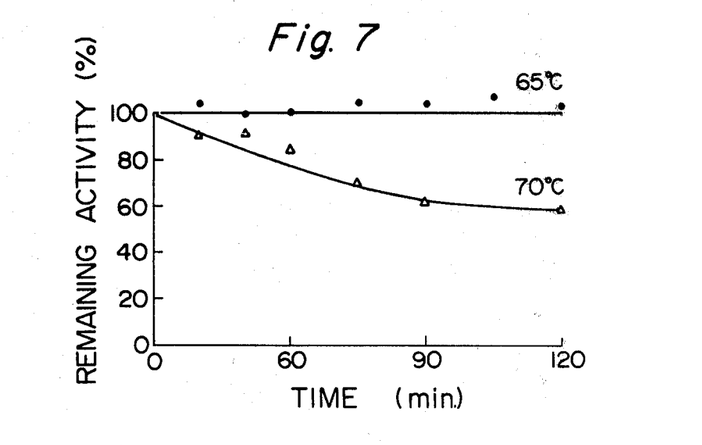

FIG. 7 of the accompanying drawings shows the heat stability at 65° C. and 70° C. of the collagenase obtained from MY-103, which was measured in the same way as described hereinabove in "3. Heat stability".

What we claim is:

1. A process for producing thermophilic collagenase, which comprises aerobically cultivating a thermophilic collagenase-producing thermophilic bacterium in a culture medium therefor, said thermophilic collagenase-producing thermophilic bacterium being a thermophilic bacterium of the genus Bacillus which grows at a temperature of 42° to 74° C. and a pH of 5.0 to 9.0, and recovering thermophilic collagenase from the culture broth, said thermophilic collagenase being such that it does not substantially lose collagenase activity even when maintained for one hour at a temperature of 60° C. in the presence of a calcium ion at a pH in the range of 6.5 to 8.5, and has a molecular weight, determined by gel filtration, between those of cytochrome C and ovalbumin.

2. The process of claim 1 wherein the collagenase-producing bacterium is a bacterium of the genus Bacillus which has the ability to assimilate polypeptides containing glycine units and proline units.

3. The process of claim 1 wherein the collagenase-producing bacterium of the genus Bacillus is Bacillus sp. nov. MY-101, Bacillus sp. nov. MY-102, or Bacillus sp. nov. MY-103.

4. The process of claim 1 wherein the cultivation is carried out in a culture medium containing a polypeptide having glycine units and proline units.

5. The process of claim 4 wherein the polypeptide is collagen or gelatin.

6. The process of claim 1 wherein the cultivation is carried out in a culture medium in which at least one divalent metal ion is present.

7. The process of claim 1 wherein the cultivation is carried out in a culture medium in which at least one metal ion selected from $Ca^{2+}$, $Mg^{2+}$ and $Mn^{2+}$ is present.

8. The process of claim 1 wherein a collagenase-producing bacterium selected from the group consisting of Bacillus sp. nov. MY-101, Bacillus, sp. nov. MY-102 and Bacillus sp. nov. MY-103 is cultivated at a temperature of 40° to 75° C. in a culture medium in which at least one metal ion and a polypeptide containing glycine units and proline units are present.

9. A novel thermophilic collagenase which does not substantially lose collagenase activity even when maintained for 1 hour at a temperature of 60° C. in the presence of a calcium ion at a pH in the range of 6.5 to 8.5, and which has a molecular weight, determined by gel filtration, between those of cytochrome C and ovalbumin.

10. The novel thermophilic collagenase of claim 9 which has a molecular weight of 15,000 to 25,000.

11. The novel thermophilic collagenase of claim 9 which has the ability to hydrolyze collagen, gelatin, or collagen having an azo dye bonded thereto.

12. A biologically pure culture of a thermophilic bacterium of the genus Bacillus which has the ability to produce thermophilic collagenase and which grows at a temperature of 42° to 74° C. and a pH of 5.0 to 9.0, said thermophilic collagenase being such that it does not substantially lose collagenase activity even when maintained for one hour at a temperature of 60° C. in the presence of a calcium ion at a pH in the range of 6.5 to 8.5, and has molecular weight, determined by gel filtration, between those of cytochrom C and ovalbumin.

13. The thermophilic bacterium of the genus Bacillus of claim 12 which has the ability to assimilate polypeptides containing glycine units and proline units.

14. The thermophilic bacterium of claim 12 which is Bacillus sp. nov. MY-101, Bacillus sp. nov. MY-102, or Bacillus sp. nov. MY-103.

* * * * *